(12) United States Patent
Shuros et al.

(10) Patent No.: US 8,509,892 B2
(45) Date of Patent: Aug. 13, 2013

(54) METHOD AND APPARATUS FOR CONTROLLING ANTI-TACHYARRHYTHMIA THERAPY USING HEMODYNAMIC TOLERABILITY

(75) Inventors: Allan C. Shuros, St. Paul, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1091 days.

(21) Appl. No.: 12/487,251

(22) Filed: Jun. 18, 2009

(65) Prior Publication Data

US 2009/0318985 A1 Dec. 24, 2009

Related U.S. Application Data

(60) Provisional application No. 61/074,071, filed on Jun. 19, 2008.

(51) Int. Cl.
*A61N 1/362* (2006.01)
(52) U.S. Cl.
USPC ............................................. 607/14
(58) Field of Classification Search
USPC ........................................ 607/4, 17, 18, 14
See application file for complete search history.

(56) References Cited

U.S. PATENT DOCUMENTS

| | | | |
|---|---|---|---|
| 4,137,910 A | 2/1979 | Murphy | |
| 4,774,950 A | 10/1988 | Cohen | |
| 4,830,006 A * | 5/1989 | Haluska et al. | 607/4 |
| 5,163,429 A | 11/1992 | Cohen | |
| 5,183,040 A | 2/1993 | Nappholz et al. | |
| 5,282,840 A | 2/1994 | Hudrlik et al. | |
| 5,311,874 A | 5/1994 | Baumann et al. | |
| 5,330,505 A | 7/1994 | Cohen | |
| 5,431,685 A | 7/1995 | Alt | |
| 5,788,717 A | 8/1998 | Mann et al. | |
| 5,797,395 A | 8/1998 | Martin | |
| 5,897,575 A | 4/1999 | Wickham | |
| 5,978,707 A | 11/1999 | Krig et al. | |
| 5,999,854 A | 12/1999 | Deno et al. | |
| 6,044,298 A | 3/2000 | Salo et al. | |
| 6,101,414 A | 8/2000 | Kroll | |

(Continued)

FOREIGN PATENT DOCUMENTS

| | | |
|---|---|---|
| EP | 0310026 A2 | 4/1989 |
| EP | 1384433 A1 | 1/2004 |

(Continued)

OTHER PUBLICATIONS

M P Ingemansson, M Holm, S B Olsson Autonomic modulation of the atrial cycle length by the head up tilt test: non-invasive evaluation in patients with chronic atrial fibrillation Heart 1998 80:71-76; doi:10.1136/hrt.80.1.71.*

(Continued)

*Primary Examiner* — Brian T Gedeon
(74) *Attorney, Agent, or Firm* — Schwegman Lundberg & Woessner, P.A.

(57) ABSTRACT

A cardiac rhythm management system identifies a relationship between one or more hemodynamic parameters sensed from a patient and levels of hemodynamic tolerability of the patient. The identified relationship allows an implantable medical device to control delivery of anti-tachyarrhythmia therapy using the patient's hemodynamic tolerability during a detected tachyarrhythmia episode, in addition to classifying the detected tachyarrhythmia episode by its type and origin.

24 Claims, 8 Drawing Sheets

(56) References Cited

U.S. PATENT DOCUMENTS

| | | | |
|---|---|---|---|
| 6,217,525 | B1 | 4/2001 | Medema et al. |
| 6,278,894 | B1 | 8/2001 | Salo et al. |
| 6,314,323 | B1 | 11/2001 | Ekwall et al. |
| 6,438,408 | B1 | 8/2002 | Mulligan et al. |
| 6,493,579 | B1 | 12/2002 | Gilkerson et al. |
| 6,522,914 | B1 | 2/2003 | Huvelle |
| 6,522,925 | B1 | 2/2003 | Gilkerson et al. |
| 6,654,639 | B1 | 11/2003 | Lu |
| 6,708,058 | B2 | 3/2004 | Kim et al. |
| 6,775,572 | B2 | 8/2004 | Zhu et al. |
| 6,873,870 | B2 | 3/2005 | Ferek-Petric |
| 6,885,890 | B2 | 4/2005 | Spinelli et al. |
| 6,988,995 | B2 | 1/2006 | Zhou et al. |
| 7,010,344 | B2 | 3/2006 | Burnes et al. |
| 7,010,347 | B2 | 3/2006 | Schecter |
| 7,130,681 | B2 | 10/2006 | Gebhardt et al. |
| 7,228,173 | B2 | 6/2007 | Cazares |
| 7,239,915 | B2 | 7/2007 | Cohen |
| 7,277,750 | B2 | 10/2007 | Perschbacher et al. |
| 7,283,871 | B1 | 10/2007 | Hofstadter et al. |
| 7,349,740 | B2 | 3/2008 | Soykan et al. |
| 7,844,331 | B2 | 11/2010 | Li et al. |
| 7,930,022 | B2 | 4/2011 | Zhang et al. |
| 2003/0083703 | A1 | 5/2003 | Zhu et al. |
| 2003/0204209 | A1 | 10/2003 | Burnes et al. |
| 2003/0208240 | A1 | 11/2003 | Pastore et al. |
| 2004/0215097 | A1 | 10/2004 | Wang |
| 2004/0220634 | A1 | 11/2004 | Belk |
| 2004/0220636 | A1 | 11/2004 | Burnes |
| 2004/0230129 | A1 | 11/2004 | Haefner |
| 2005/0049646 | A1 | 3/2005 | Czygan et al. |
| 2005/0149135 | A1 | 7/2005 | Krig et al. |
| 2005/0222629 | A1 | 10/2005 | Perschbacher et al. |
| 2006/0089675 | A1 | 4/2006 | Burnes et al. |
| 2006/0122651 | A1 | 6/2006 | Whitman |
| 2006/0184060 | A1 | 8/2006 | Belalcazar et al. |
| 2006/0235326 | A1 | 10/2006 | Dzwonczyk et al. |
| 2007/0043394 | A1 | 2/2007 | Zhang et al. |
| 2007/0135848 | A1 | 6/2007 | Kim et al. |
| 2007/0142866 | A1* | 6/2007 | Li et al. ............ 607/17 |
| 2007/0149890 | A1 | 6/2007 | Li et al. |
| 2007/0173894 | A1 | 7/2007 | Li |
| 2007/0197928 | A1 | 8/2007 | Kim et al. |
| 2007/0203524 | A1 | 8/2007 | Sheldon et al. |
| 2008/0015651 | A1* | 1/2008 | Ettori et al. ............ 607/17 |
| 2008/0132800 | A1* | 6/2008 | Hettrick et al. ............ 600/509 |
| 2008/0281367 | A1 | 11/2008 | Zhang et al. |

FOREIGN PATENT DOCUMENTS

| | | | |
|---|---|---|---|
| EP | 1582233 | A2 | 10/2005 |
| EP | 1582233 | A2 | 10/2008 |
| JP | 6305763 | A | 1/1988 |
| JP | 6-508289 | A | 9/1994 |
| JP | 2004-528864 | A | 9/2004 |
| JP | 5090520 | | 9/2012 |
| WO | WO-95/19806 | A1 | 7/1995 |
| WO | WO-95/20348 | A1 | 8/1995 |
| WO | WO-03/090858 | A1 | 11/2003 |
| WO | WO-2004/084989 | A1 | 10/2004 |
| WO | WO-2004/091719 | A2 | 10/2004 |
| WO | WO-2004/098389 | A2 | 11/2004 |
| WO | WO-2006/041337 | A1 | 4/2006 |
| WO | WO-2006/088805 | A2 | 8/2006 |
| WO | WO-2007/078421 | A2 | 7/2007 |
| WO | WO-2008/137166 | A1 | 11/2008 |
| WO | WO-2009/064222 | A1 | 5/2009 |
| WO | WO-2009/154758 | A2 | 12/2009 |

OTHER PUBLICATIONS

"European Application Serial No. 08767613.6, Response filed Aug. 23, 2011 to Office Action dated Apr. 29, 2011", 13 pgs.
"European Application Serial No. 09767071.5, Office Action mailed Feb. 10, 2011", 2 pgs.
"European Application Serial No. 09767071.5, Response filed Mar. 10, 2011 to Office Action mailed Feb. 10, 2011", 11 pgs.
"Japanese Application Serial No. 2011-514612, Amendment filed Jan. 5, 2011", (w/ English Translation of Amended Claims), 12 pgs.
"U.S. Appl. No. 11/132,082, Final Office Action mailed Jan. 8, 2009", 15 pgs.
"U.S. Appl. No. 11/132,082, Final Office Action mailed Oct. 8, 2008", 14 pgs.
"U.S. Appl. No. 11/132,082, Non-Final Office Action mailed May 20, 2008", 14 pgs.
"U.S. Appl. No. 11/132,082, Response filed Mar. 9, 2009 to Final Office Action mailed Jan. 8, 2009", 18 pgs.
"U.S. Appl. No. 11/132,082, Response filed Aug. 20, 2008 to Non-Final Office Action mailed May 20, 2008", 20 pgs.
"U.S. Appl. No. 11/132,082, Response filed Dec. 15, 2008 to Final Office Action mailed Oct. 8, 2008", 18 pgs.
"U.S. Appl. No. 11/312,082, Advisory Action mailed Mar. 20, 2009", 3 pgs.
"U.S. Appl. No. 11/312,082, Advisory Action mailed Aug. 31, 2009", 3 pgs.
"U.S. Appl. No. 11/312,082, Final Office Action mailed Jun. 1, 2009", 15 pgs.
"U.S. Appl. No. 11/312,082, Final Office Action mailed Nov. 19, 2009", 15 pgs.
"U.S. Appl. No. 11/312,082, Response filed Aug. 3, 2009 to Final Office Action mailed Jun. 1, 2009", 18 pgs.
"U.S. Appl. No. 11/745,016, Final Office Action mailed Jan. 13, 2010", 9 pgs.
"U.S. Appl. No. 11/745,016, Non-Final Office Action mailed Jun. 26, 2009", 10 pgs.
"U.S. Appl. No. 11/745,016, Response filed Sep. 28, 2009 to Office Action mailed Jun. 26, 2009", 13 pgs.
"European Application Serial No. 06837139.2, Communication mailed Apr. 22, 2009", 3 pgs.
"European Application Serial No. 06837139.2, Response filed Sep. 1, 2009 to Communication dated Apr. 22, 2009", 15 pgs.
"International Application Serial No. PCT/US2006/043459, International Search Report mailed Oct. 23, 2007", 7 pgs.
"International Application Serial No. PCT/US2006/043459, Partial International Search Report mailed Mar. 14, 2007", 6 pgs.
"International Application Serial No. PCT/US2006/043459, Written Opinion mailed Oct. 23, 2007", 13 pgs.
"International Application Serial No. PCT/US2008/005832, International Search Report mailed Sep. 18, 2008", 5 pgs.
"International Application Serial No. PCT/US2008/005832, Written Opinion mailed Sep. 18, 2008", 9 pgs.
"Japanese Application Serial No. 2008-547229, Amended Claims filed Oct. 26, 2009", (w/ English Translation), 10 pgs.
Fallert, M. A., et al., "Myocardial Electrical Impedance Mapping of Ischemic Sheep Hearts and Healing Aneurysms", *Circulation* 87(1), (Jan. 1993), 199-207.
Kaye, G., et al., "Can transventricular intracardiac impedance measurement discriminate haemodynamically unstable ventricular arrhythmias in human?", *Europace*, 9 (2), (2007), 122-126
Kaye, G., et al., "The use of unipolar intracardiac impedance for discrimination of haemodynamically stable and unstable arrhythmias in man.", *Eurospace*, 8(11), (2006), 988-993.
Khoury, D., et al., "Continuous right ventricular volume assessment by catheter measurement of impedance for antitachycardia system control.", *Pacing Clin Electrophysiol.*, 12(12), (Dec. 1989), 1918-1926.
Salazar, Y., et al., "Transmural Versus Nontransmural In Situ Electrical Impedance Spectrum for Healthy, Ischemic, and Healed Myocardium.", *IEEE Transactions on Biomedical Engineering*, 51(8), (2004), 1421-1427.
Steinbach, K. K, et al., "Hemodynamics during ventricular tachyarrhythmias", *American Heart Journal*, 127(4, Part 2), (Apr. 1994), 1102-1106.
Wood, M. A., et al., "Comparison of Right Ventricular Impedance, Pulse Pressure and Maximal dP/dt for Determination of Hemodynamic Stability of Ventricular Arrhythmias Associated with Coronary Artery Disease", *Am J Cardiol.*, 66(5), (Sep. 1, 1990), 575-582.
"Japanese Application Serial No. 2008-547229, Notice of Reasons for Rejection mailed Nov. 30, 2011", (w/ English Translation), 5 pgs.

"Japanese Application Serial No. 2008-547229, Response filed Feb. 29, 2012 to Office Action mailed Nov. 30, 2011", (w/ English Translation of Amended Claims), 11 pgs.

"Japanese Application Serial No. 2010-506339, Office Action mailed Dec. 6, 2011", (w/ English Translation), 6 pgs.

"Japanese Application Serial No. 2010-506339, Response filed Feb. 29, 2012 to Office Action mailed Dec. 6, 2011", (w/ English Translation of Claims), 9 pgs.

"U.S. Appl. No. 11/312,082, Examiner Interview Summary mailed May 21, 2010", 3 pgs.

"U.S. Appl. No. 11/312,082, Final Office Action mailed Feb. 5, 2010", 14 pgs.

"U.S. Appl. No. 11/312,082, Notice of Allowance mailed Jul. 29, 2010", 6 pgs.

"U.S. Appl. No. 11/312,082, Response filed Jan. 19, 2010 to Final Office Action mailed Nov. 19, 2009", 19 pgs.

"U.S. Appl. No. 11/312,082, Preliminary Amendment filed May 26, 2010", 16 pgs.

"U.S. Appl. No. 11/312,082, Response filed May 5, 2010 to Final Office Action mailed Feb. 5, 2010", 19 pgs.

"U.S. Appl. No. 11/745,016, Examiner Interview Summary mailed Apr. 23, 2010", 3 pgs.

"U.S. Appl. No. 11/745,016, Examiner interview Summary mailed Sep. 30, 2009", 2 pgs.

"U.S. Appl. No. 11/745,016, Non-Final Office Action mailed May 14, 2010", 11 pgs.

"U.S. Appl. No. 11/745,016, Notice of Allowance mailed Dec. 14, 2010, ", 12 pgs.

"U.S. Appl. No. 11/745,016, Response filed May 4, 2010 to Final Office Action mailed Jan. 13, 2010", 13 pgs.

"U.S. Appl. No. 11/745,016, Response filed Sep. 14, 2010 to Non Final Office Action mailed May 14, 2010", 13 pgs.

"European Application Serial No. 08767613.6, Office Action mailed Apr. 29, 2011", 3 pgs.

"International Application Serial No. PCT/US2009/03638, International Search Report mailed Feb. 24, 2010", 5 pgs.

"International Application Serial No. PCT/US2009/03638, Written Opinion mailed Feb. 24, 2010", 9 pgs.

Greene, H., et al., "Termination of ventricular tachycardia by programmed extrastimuli from an externally-activated permanent pacemaker", *Pacing and Clinical Electrophysiology*, 5(3), (1982), 434-439.

Lee, C., et al., "Decision Boundary Feature Extraction for Nonparametric Classification", *IEEE Transactions on Systems, Man and Cybernetics*, 23(2), (1993), 433-444.

"Japanese Application Serial No. 2011-514612, Office Action mailed Sep. 28, 2012", With English Translation, 5 pgs.

"Japanese Application Serial No. 2011-514612, Response filed Dec. 19, 2012 to Office Action mailed Sep. 28, 2012", English Claims, 8 pgs.

\* cited by examiner

METHOD AND APPARATUS FOR CONTROLLING ANTI-TACHYARRHYTHMIA THERAPY USING HEMODYNAMIC TOLERABILITY

CROSS-REFERENCE TO RELATED APPLICATION

This application claims the benefit of U.S. Provisional Application No. 61/074,071, filed on Jun. 19, 2008, under 35 U.S.C. §119(e), which is hereby incorporated by reference.

TECHNICAL FIELD

This document relates generally to medical devices and particularly to a cardiac rhythm management (CRM) system that determines a patient's hemodynamic tolerability during tachyarrhythmia for controlling delivery of anti-tachyarrhythmia therapy.

BACKGROUND

Tachyarrhythmias are abnormal heart rhythms characterized by a rapid heart rate. Tachyarrhythmia generally includes supraventricular tachyarrhythmia and ventricular tachyarrhythmia. Fibrillation is a form of tachyarrhythmia further characterized by an irregular heart rhythm. In a normal heart, the sinoatrial (SA) node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. Ventricular tachyarrhythmia occurs when the electrical impulses propagate along a pathologically formed self-sustaining conductive loop within the ventricles or when a biologic pacemaker (focus) in a ventricle usurps control of the heart rate from the SA node. When the atria and the ventricles become dissociated during ventricular tachyarrhythmia, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Ventricular cardioversion and defibrillation are used to terminate most ventricular tachyarrhythmias, including ventricular tachycardia (VT), and VF. An implantable cardioverter/defibrillator (ICD) is a CRM device that delivers cardioversion/defibrillation pulses, each being an electric shock, to terminate a detected tachyarrhythmia episode by depolarizing the entire myocardium simultaneously and rendering it refractory. Another type of electrical therapy for tachyarrhythmia is ATP, including atrial ATP for treating atrial tachyarrhythmia and ventricular ATP for treating ventricular tachyarrhythmia. In ATP, the heart is competitively paced in an effort to interrupt the reentrant loop causing the tachyarrhythmia. Many ICDs include both ATP and cardioversion/defibrillation capabilities.

The delivery of each cardioversion/defibrillation pulse consumes a considerable amount of power and results in patient discomfort owing to the high voltage of the shock pulses. Additionally, if delivered during the atrial vulnerable period, a cardioversion/defibrillation pulse may also cause atrial fibrillation. Thus, it is desirable to apply a cardioversion/defibrillation only when it is necessary. For example, depending on the type and origin of a tachyarrhythmia as well as the patient's own conditions, the tachyarrhythmia may be terminated with an ATP therapy and/or monitored for a certain period of time to determine whether a cardioversion/defibrillation therapy is to be delivered. However, on the other hand, when a ventricular cardioversion/defibrillation therapy is necessary, the consequence of failure to deliver the therapy timely can be fatal. Therefore, there is a need for an accurate determination of whether an anti-tachyarrhythmia therapy, such as a cardioversion/defibrillation therapy, should be delivered in response to each detected tachyarrhythmia episode.

SUMMARY

A CRM system identifies a relationship between one or more hemodynamic parameters sensed from a patient and levels of hemodynamic tolerability of the patient. The identified relationship allows an ICD to control delivery of anti-tachyarrhythmia therapy using the patient's hemodynamic tolerability during a detected tachyarrhythmia episode, in addition to classifying the detected tachyarrhythmia episode by its type and origin.

In one embodiment, a CRM system includes a hemodynamic tolerability analyzer and a control circuit. The hemodynamic tolerability analyzer includes a hemodynamic parameter input, an annotation input, and a hemodynamic tolerability map generator. The hemodynamic parameter input receives values of one or more hemodynamic parameters, including values of the one or more hemodynamic parameters sensed during delivery of pacing pulses according to a hemodynamic challenge protocol. The annotation input receives annotations associating the values of the one or more hemodynamic parameters to levels of hemodynamic tolerability. The levels of hemodynamic tolerability are each a measure of tolerance to deteriorated hemodynamic performance resulting from tachyarrhythmia caused by the delivery of pacing pulses. The hemodynamic tolerability map generator generates a hemodynamic tolerability map relating at least the values of the one or more hemodynamic parameters to the levels of hemodynamic tolerability. The control circuit controls the delivery of pacing pulses by executing the hemodynamic challenge protocol.

In one embodiment, a method for operating a CRM system is provided. The CRM system includes an implantable system and an external system communicatively coupled to the implantable system. According to the method, pacing pulses are delivered to induce various degrees of tachyarrhythmia in a patient. Values of one or more hemodynamic parameters acquired from the patient during the delivery of the pacing pulses are received. The patient is monitored for hemodynamically compromising symptoms corresponding to levels of hemodynamic tolerability, which are each a measure of the patient's tolerance to deteriorated hemodynamic performance resulting from tachyarrhythmia induced by the pacing pulses. A hemodynamic tolerability map is generated to relate at least the received values of the one or more hemodynamic parameters to the levels of hemodynamic tolerability.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
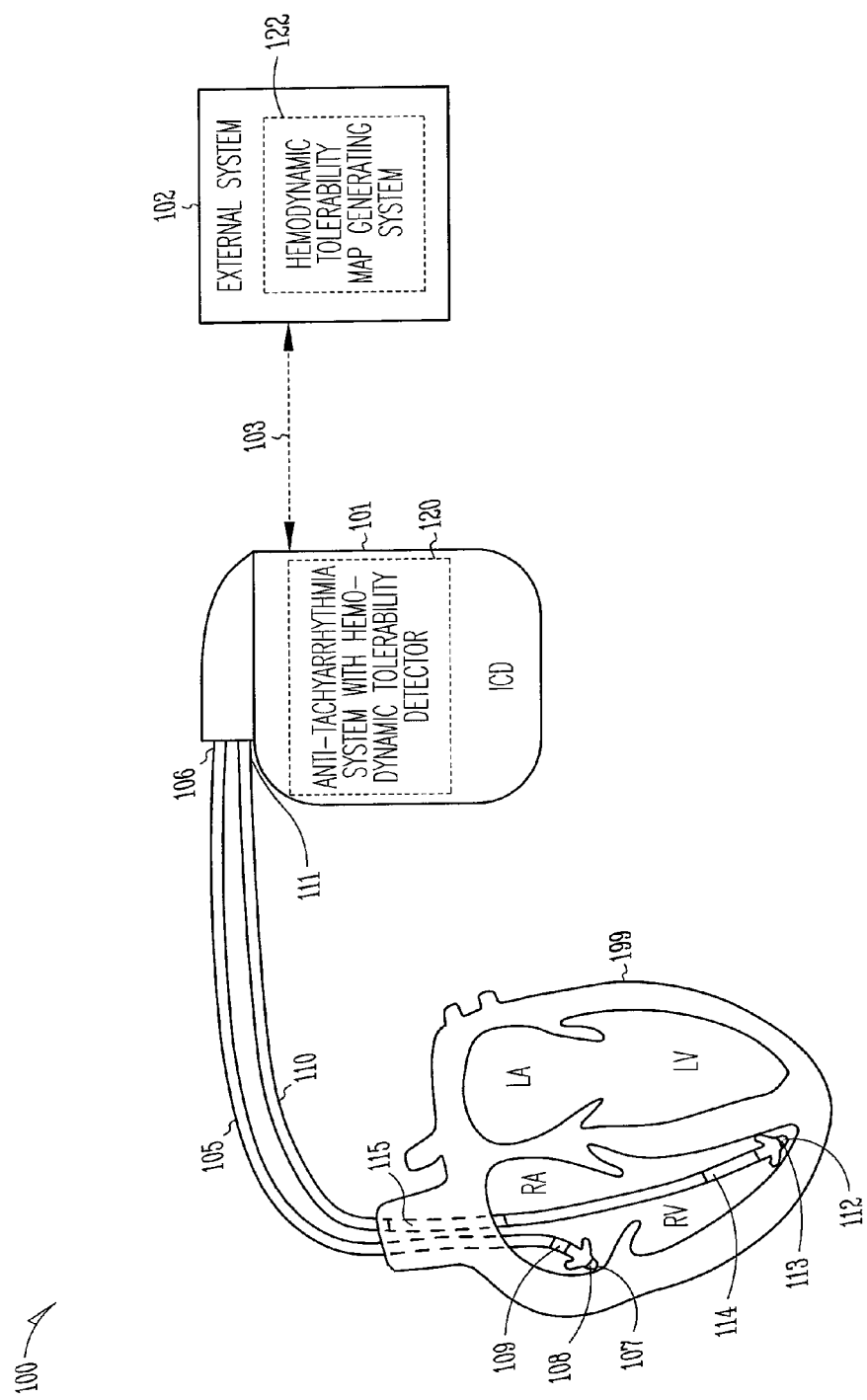
FIG. 1 is an illustration of an embodiment of a CRM system and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a system that evaluates a patient's hemodynamic tolerability and controls delivery of anti-tachyarrhythmia therapy to the patient using the result. One way to determine whether to deliver an anti-tachyarrhythmia therapy in response to a detected tachyarrhythmia episode is to classify the detected tachyarrhythmia episode by analyzing one or more electrograms. For example, using heart rate detected from various heart chambers and morphology of electrogram waveforms, a tachyarrhythmia episode is detected and classified by its type (such as tachycardia and fibrillation) and origin (such as supraventricular and ventricular). However, the type and origin of tachyarrhythmia do not always indicate the necessity for a ventricular anti-tachyarrhythmia therapy such as a ventricular defibrillation shock. A more clinically relevant criterion for determining the necessity and/or appropriateness of a ventricular anti-tachyarrhythmia therapy is the patient's hemodynamic tolerability to the tachyarrhythmia. Hemodynamic tolerability is the patient's tolerance to deteriorated hemodynamic performance resulting from tachyarrhythmia. In one embodiment, hemodynamic tolerability is measured by hemodynamically compromising symptoms experienced by the patient in association with values of one or more hemodynamic parameters measured from the patient. Different patients have different levels of hemodynamic tolerability to tachyarrhythmia. Therefore, in addition to detecting and classifying a tachyarrhythmia episode, it is desirable to determine whether an anti-tachyarrhythmia therapy is to be delivered based on the hemodynamic tolerability individually evaluated for each patient.

A physician familiar with a patient's hemodynamic tolerability can factor it into the programming of an ICD for determining when to deliver an anti-tachyarrhythmia therapy to the patient. However, this depends on the physician's knowledge and experience with the patient and the ICD. To provide a standardized approach to programming an ICD using the patient's hemodynamic tolerability, the present system executes a hemodynamic challenge protocol to induce hemodynamically compromising effects for evaluating the patient's response to these effects. In one embodiment, cardiac pacing is delivered to induce the hemodynamically compromising effects according to the hemodynamic challenge protocol. While pacing rate is increased incrementally to induce tachyarrhythmia with increasing degree of severity in the patient, one or more hemodynamic parameters are monitored, and hemodynamically compromising effects such as dizziness, angina, weakness, and syncope are recorded in association with the values of the one or more hemodynamic parameters. In various embodiments, the present system provides personalized symptomatic response information to guide programming of ICDs to enhance tachyarrhythmia discrimination and reduce unnecessary and inappropriate deliveries of anti-tachyarrhythmia therapies.

In this document, the relationship between a heart rate and a cardiac cycle length (also known as cardiac interval) is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a tachyarrhythmic heart rate, and a "slow beat" is a heart beat having a heart rate that is not tachyarrhythmic.

FIG. 1 is an illustration of an embodiment of a CRM system 100 and portions of the environment in which CRM system 100 is used. CRM system 100 includes an implantable system with at least an ICD 101 and implantable leads 105 and 110. After implantation into a patient, ICD 101 is electrically coupled to the patient's heart 199 through implantable leads 105 and 110. An external system 102 communicates with ICD 101 via a telemetry link 103.

ICD 101 is an implantable medical device that performs CRM functions including delivery of cardiac pacing and cardioversion/defibrillation therapies. ICD 101 includes a hermetically sealed can housing an electronic circuit that senses physiological signals and delivers therapeutic electrical pulses. The hermetically sealed can may also function as an electrode for sensing and/or pulse delivery purposes. In the illustrated embodiment, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to ICD 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow for sensing of the atrial electrogram and/or delivery of atrial pacing pulses. Lead 110 is a defibrillation lead that includes a proximal end 111 connected to ICD 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 and 114 allow for sensing of the ventricular electrogram and/or delivery of ventricular pacing pulses. Electrodes 114 and 115 allow for delivery of ventricular cardioversion/defibrillation pulses. The arrangement and functions of these leads and electrodes are discussed above by way of example and not by way of limitation. Other ways of arranging and using such leads and electrodes are possible, depending on the need of the patient and the capability of the ICD, as understood by those skilled in the art. In one embodiment, in addition to leads 105 and 110, ICD 101 connects to another pacing lead with a distal end placed in the coronary sinus or coronary vein over the left ventricle (LV) to allow for delivery of pacing pulses to the LV.

ICD 101 includes an anti-tachyarrhythmia system 120 providing for control and delivery of anti-tachyarrhythmia therapies including ATP and cardioversion/defibrillation therapies. Anti-tachyarrhythmia system 120 includes a hemodynamic tolerability detector that detects the patient's level of hemodynamic tolerability using one or more hemodynamic parameters sensed from the patient. In one embodiment, in response to a tachyarrhythmia detected and classified as a type indicated for an anti-tachyarrhythmia therapy such as ventricular defibrillation, anti-tachyarrhythmia system 120 further determines whether to deliver the anti-tachyarrhythmia therapy based on whether the detected tachyarrhythmia is considered hemodynamically tolerable to the patient. Anti-tachyarrhythmia therapies, especially defibrillation shocks, are delivered only when the detected tachyarrhythmia is considered hemodynamically intolerable. Details of anti-tachyarrhythmia system 120 is discussed below, with reference to FIGS. 4 and 5.

External system 102 allows for programming of ICD 101 and receives signals acquired by ICD 101. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system provides for access to ICD 101 from a remote location, such as for monitoring patient status and/or adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101 (such as the one or more hemodynamic parameters), extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), and programming ICD 101 to deliver pacing and/or cardioversion/defibrillation therapies.

In the illustrated embodiment, external system 102 includes a hemodynamic tolerability map generating system 122. ICD 101 is programmed using external system 102 to deliver pacing pulses to heart 199 by executing a hemodynamic challenge protocol for inducing increasingly severe tachyarrhythmia for hemodynamic tolerability map generating system 122 to identify a relationship between one or more hemodynamic parameters sensed from the patient and levels of hemodynamic tolerability specified by the patient's various detectable hemodynamically compromising symptoms. A hemodynamic tolerability map is generated to represent this identified relationship. In this document, a "hemodynamic tolerability map" represents the relationship between the one or more hemodynamic parameters and the levels of hemodynamic tolerability recorded in any format and stored in any form of medium. The hemodynamic tolerability map is then stored in ICD 101 for detecting the patient's level of hemodynamic tolerability during a detected tachyarrhythmia episode to determine whether an anti-tachyarrhythmia therapy is to be delivered to terminate the detected tachyarrhythmia episode. Details of hemodynamic tolerability map generating system 122 is discussed below, with reference to FIGS. 2 and 3.

In various embodiments, the circuit of ICD 101 and external system 102, including their various elements discussed in this document, are implemented using a combination of hardware and software. In various embodiments, each element of ICD 101 and external system 102 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 2:
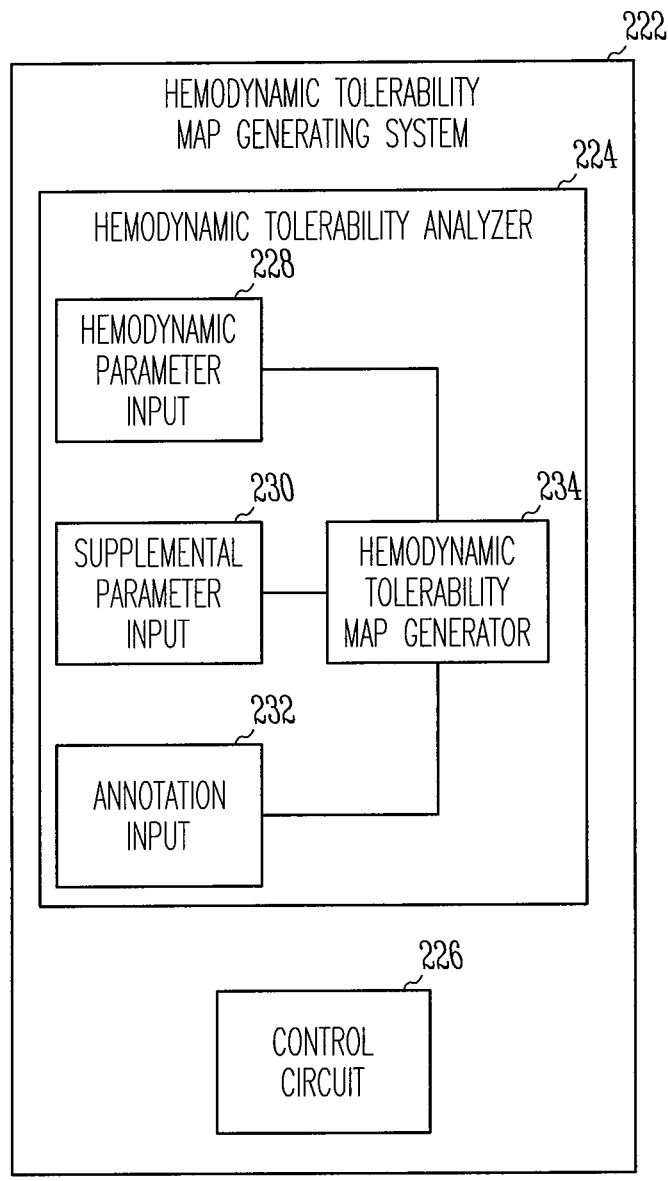
FIG. 2 is a block diagram illustrating an embodiment of a system for generating a hemodynamic tolerability map.

FIG. 2 is a block diagram illustrating an embodiment of a hemodynamic tolerability map generating system 222. Hemodynamic tolerability map generating system 222 is an embodiment of hemodynamic tolerability map generating system 122 and includes a hemodynamic tolerability analyzer 224 and a control circuit 226.

Hemodynamic tolerability analyzer 224 generates a hemodynamic tolerability map relating values of at least one or more hemodynamic parameters sensed from a patient to levels of hemodynamic tolerability of the patient. The values of the one or more hemodynamic parameters include values sensed during delivery of pacing pulses according to a hemodynamic challenge protocol for inducing various degrees of tachyarrhythmia in the patient. In the illustrated embodiment, hemodynamic tolerability analyzer 224 includes a hemodynamic parameter input 228, a supplemental parameter input 230, an annotation input 232, and a hemodynamic tolerability map generator 234. When one or more supplemental parameters are considered to substantially affect the values of the one or more hemodynamic parameters and/or the levels of hemodynamic tolerability, the hemodynamic tolerability map relates the values of the one or more hemodynamic parameters and the values of one or more supplemental parameters to the levels of hemodynamic tolerability.

Hemodynamic parameter input 228 receives the values of the one or more hemodynamic parameters. In one embodiment, the values of the one or more hemodynamic parameters include values transmitted from ICD 101 via telemetry link 103 in real time. Examples of such hemodynamic parameters include parameters derived from intracardiac impedance, transthoracic impedance, arterial pressure, pulmonary artery pressure (PAP), RV pressure, LV coronary pressure, LV coronary temperature, and level of blood oxygen saturation, such as the amplitude, derivative (rate of change), and morphology of each of these signals. In one embodiment, the values of the one or more hemodynamic parameters received by hemodynamic parameter input 228 include values of stroke impedance, which is the difference between a maximum value and a minimum value of the intracardiac or transthoracic impedance over a cardiac cycle. In one embodiment, the values of the one or more hemodynamic parameters received by hemodynamic parameter input 228 include values of a composite hemodynamic parameter calculated using a plurality of hemodynamic parameters. In a specific embodiment, the composite hemodynamic parameter is calculated using the plurality of hemodynamic parameters and a plurality of weighting factors each associated with a hemodynamic parameter of the plurality of hemodynamic parameters. The weighting factors are approximately optimized to produce a clear distinction between the levels of hemodynamic tolerability as indicated by the composite hemodynamic parameter. In one embodiment, the values of the one or more hemodynamic parameters are each derived from one or more hemodynamic parameters and one or more other physiological parameters.

Supplemental parameter input 230 receives values of the one or more supplemental parameters, which are parameters indicative of factors substantially affecting the values of the one or more hemodynamic parameters and/or the levels of the hemodynamic tolerability. In one embodiment, the values of the one or more supplemental parameters include values transmitted from ICD 101 via telemetry link 103 in real time. In one embodiment, the values of the one or more supplemental parameters received by supplemental parameter input 230 include values of a position parameter indicative of whether the patient is in a supine position or an upright position. In another embodiment, the values of the one or more supplemental parameters received by supplemental parameter input 230 include values of a heart rate.

Annotation input 232 receives annotations associating the patient's levels of hemodynamic tolerability to at least the values of the one or more hemodynamic parameters. The levels of hemodynamic tolerability are each a measure of tolerance to deteriorated hemodynamic performance resulting from tachyarrhythmia. When one or more supplemental parameters are considered to substantially affect the values of the one or more hemodynamic parameters and/or the levels of hemodynamic tolerability, the annotations associate the levels of hemodynamic tolerability to the values of the one or more hemodynamic parameters and the values of the one or more supplemental parameters. In one embodiment, the annotations include markers each indicative of one of the patient's levels of hemodynamic tolerability. Threshold values of at least the one or more hemodynamic parameters representing the levels of the patient's hemodynamic tolerability are established as the values of the one or more hemodynamic parameters associated with the markers. In a further embodiment, the annotations include notes written by a user such as a physician or other caregiver operating CRM system 100. In one embodiment, the levels of hemodynamic tolerability are specified by the hemodynamically compromising symptoms, with each level corresponding to a specified type symptom or its detectable indication. Examples of such predetermined type symptoms include dizziness, angina, weakness, and syncope, as monitored by the physician or other caregiver and/or indicated by the patient. Some of these symptoms are monitored by their visible indications such as consciousness, pupil dilation, and tremor.

Hemodynamic tolerability map generator 234 generates the hemodynamic tolerability map. In one embodiment, the hemodynamic tolerability map relates at least the threshold values of the one or more hemodynamic parameters to the levels of hemodynamic tolerability. In other words, each level of hemodynamic tolerability is specified by at least one threshold value of the one or more hemodynamic parameters. In one embodiment, the map relates value ranges (such as ranges each specified by two threshold values) of the one or more hemodynamic parameters to the levels of hemodynamic tolerability. In one embodiment, the threshold values of the one or more hemodynamic parameters are functions of the one or more supplemental parameters. For example, when the one or more supplemental parameters include the position parameter indicative of whether the patient is in the supine position or the upright position, a set of threshold values is identified for the one or more hemodynamic parameters with the patient in the supine position, and another set of threshold values is identified for the one or more hemodynamic parameters with the patient in the upright position. The hemodynamic tolerability map relates these two sets of threshold values to the levels of hemodynamic tolerability.

In one embodiment, the threshold values of the one or more hemodynamic parameters in the hemodynamic tolerability map include values estimated by interpolation using the received values of the one or more hemodynamic parameters, to increase the resolution of the map and/or simplifying the map generation process. For example, a value "A" of a hemodynamic parameter is found to correspond to a level "A" of hemodynamic tolerability (e.g., dizziness), and a value "C" of a hemodynamic parameter is found to correspond to a level "C" of hemodynamic tolerability (e.g., syncope). Then, the average value "B" (which is (A+C)/2) corresponds to a level "B" of hemodynamic tolerability that is between levels "A" and "C" (e.g., halfway between dizziness and syncope). In one embodiment, the threshold values of the one or more hemodynamic parameters in the hemodynamic tolerability map include values estimated by extrapolation using the received values of the one or more hemodynamic parameters, to expand the range of the map while simplifying the map generation process and/or avoiding induction of severe hemodynamic challenges that raises patient safety concerns. For example, when cardiac pacing alone is incapable of inducing syncope or pre-syncope in a patient, extrapolation eliminates the need to induce VF in the patient by delivering a defibrillation shock.

In one embodiment, the hemodynamic tolerability map is generated for each individual patient using data collected during execution of the hemodynamic challenge protocol for the that patient. The generated hemodynamic tolerability map is then transmitted to ICD 101 for controlling delivery of anti-tachyarrhythmia therapies to the patient. In another embodiment, the hemodynamic tolerability map is generated for each individual patient using data collected during execution of the hemodynamic challenge protocol for the that patient as well as data collected during spontaneous hemodynamic challenge events experienced by the patient. For example, ICD 101 records detected tachyarrhythmia episodes and/or other symptoms and values of the one or more hemodynamic parameters during the tachyarrhythmia episodes. Such recorded information can be used in the generation of the hemodynamic tolerability map. In one embodiment, after a hemodynamic tolerability map is initially generated and transmitted to ICD 101, information recorded during the use of ICD 101 is used to update the stored hemodynamic tolerability map as needed such that the map remains current with the patient's changing conditions.

Control circuit 226 controls programming of ICD 101 for delivery of pacing pulses by executing the hemodynamic challenge protocol. The hemodynamic challenge protocol is produced to induce increasingly severe tachyarrhythmia by delivering pacing pulses at an increasing pacing rate. In various embodiments, the hemodynamic challenge protocol is designed for expanding the range of the values of the one or more hemodynamic parameters and inducing various symptoms corresponding to the levels of hemodynamic tolerability. These symptoms are detectable by the physician or other caregiver and/or the patient. In one embodiment, ICD 101 is used to terminate the induced tachyarrhythmia when necessary.

In one embodiment, the various symptoms are induced by using various combinations of pacing parameters specifying pacing sites, pacing modes, pacing rates, and pacing time intervals. Examples of selectable pacing sites include RA, RV apex, RV outflow tract, and LV. Examples of selectable pacing modes include AAI, VVI, DDD, and cardiac resynchronization therapy (CRT) overdrive pacing modes. Examples of pacing time intervals include atrioventricular (AV) delay and interventricular (LV-RV) delay. The various combinations of such pacing parameters allow induction of a wide variety of symptoms corresponding to a wide range of the levels of hemodynamic tolerability. In one embodiment, in addition to cardiac pacing, other techniques are used to induce the symptoms for expanding the range of evaluation. Examples of such techniques include delivering defibrillation shock to induce VT or VF, exercising, and psychologically increasing stress on the patient.

Figure 3:
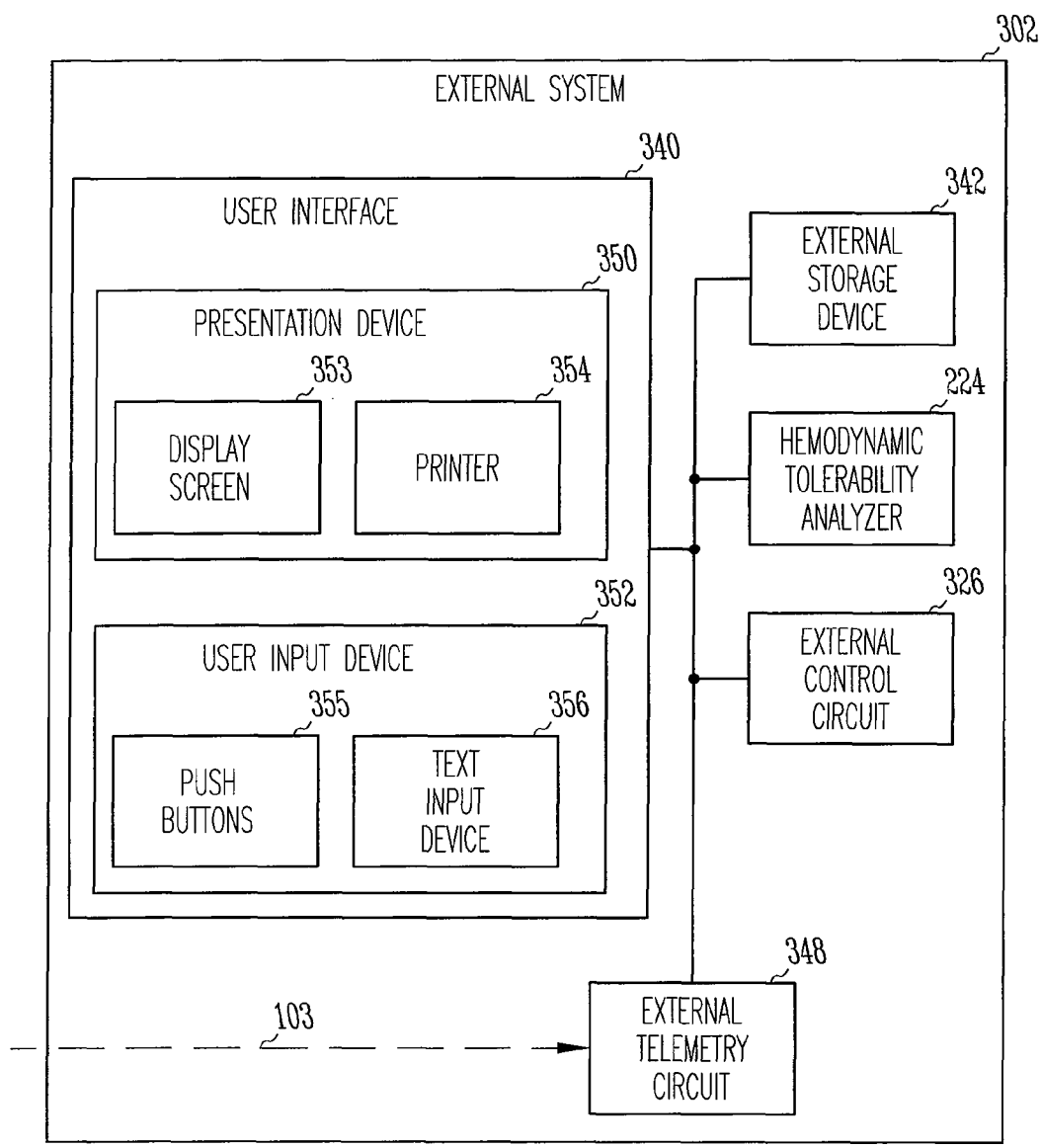
FIG. 3 is a block diagram illustrating an embodiment of an external system of the CRM system.

FIG. 3 is a block diagram illustrating an embodiment of an external system 302. External system 302 is an embodiment of external system 102 and includes a user interface 340, an external storage device 342, hemodynamic tolerability analyzer 224, an external control circuit 326, and an external telemetry circuit 348.

User interface 340 includes a presentation device 350 and a user input device 352. Presentation device 350 presents the values of the one or more hemodynamic parameters and the values of the one or more supplemental parameters (if acquired). In one embodiment, presentation device 350 presents the annotations entered by the user, including the markers, in association with the values of the one or more hemodynamic parameters and the values of the one or more supplemental parameters (if acquired). In various embodiments, presentation device 350 includes one or more of a display screen 353 and a printer 354. User input device 352 receives the annotations from the user and records the annotations in association with the values of the one or more hemodynamic parameters and the values of the one or more supplemental parameters (if acquired). In one embodiment, user input device 352 includes one or more push buttons 355 that are mechanical push button switches and/or buttons displayed on an interactive screen. In one embodiment, user input device 352 includes a plurality of buttons each corresponding to one of the levels of hemodynamic tolerability. For example, the buttons are each labeled as one of the specified symptoms such as dizziness, angina, weakness, and syncope. In the illustrated embodiment, user input device 352 also includes a text input device 356 that allow the user to write notes.

External storage device 342 provides for storage of the hemodynamic challenge protocol and the hemodynamic tolerability map. External control circuit 326 controls the operation of external system 302 and includes the functions of control circuit 226. External telemetry circuit 348 transmits data to and receives data from ICD 101.

In one embodiment, the process of generating the hemodynamic tolerability map is similar to an exercise test in which the severity of a patient' symptom is ranked by exercise tolerance, known as the Borg scale. In the illustrated embodiment, hemodynamic tolerability analyzer 224 is part of external system 302. In another embodiment, hemodynamic tolerability analyzer 224 is part of ICD 101, when the levels of hemodynamic tolerability are automatically detectable using implantable sensors replacing annotation input 232.

Figure 4:
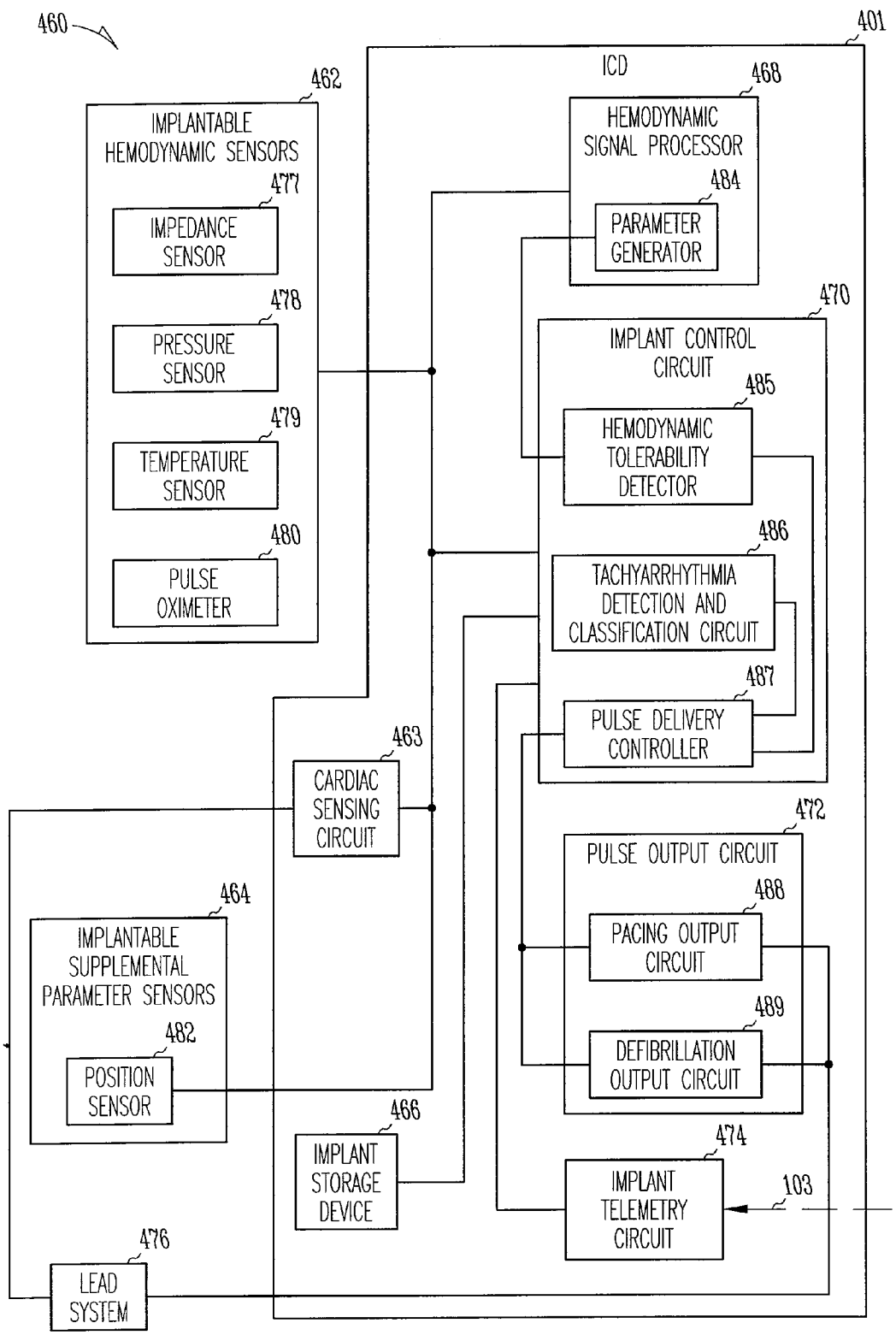
FIG. 4 is a block diagram illustrating an embodiment of an implantable system of the CRM system.

FIG. 4 is a block diagram illustrating an embodiment of an implantable system 460. Implantable system 460 is an embodiment of the implantable system of CRM system 100 and includes an implantable hemodynamic sensor 462, an implantable supplemental parameter sensor 464, an ICD 401, and a lead system 476. In various embodiments, portions of implantable hemodynamic sensor 462 and/or portions of implantable supplemental parameter sensor 464 are incorporated into one or both of ICD 401 and lead system 476.

Implantable hemodynamic sensor 462 senses hemodynamic signals, or signals indicative of hemodynamic performance. In the illustrated embodiment, implantable hemodynamic sensor 462 includes an impedance sensor 477 that senses an intracardiac or transthoracic impedance signal, a pressure sensor 478 that senses a blood pressure signal, a temperature sensor 479 that senses an intravascular temperature, and a pulse oximeter 480 that senses an oximetry signal indicative of the level of blood oxygen saturation. In other embodiments, implantable hemodynamic sensor 462 includes any one or more of impedance sensor 477, pressure sensor 478, temperature sensor 479, and pulse oximeter 480. In one embodiment, temperature sensor 479 senses an LV coronary vein temperature. In various embodiments, pressure sensor 478 includes one or more of an intravascular pressure sensor to sense an arterial pressure, an extravascular strain sensor to sense an strain indicative of the arterial pressure, a PAP sensor configured to be placed in the pulmonary artery to sense a PAP signal, a RV pressure sensor configured to be placed in the RV to sense an RV pressure signal, and an LV coronary pressure sensor configured to be placed in the coronary artery over the LV to sense an LV coronary pressure signal.

Implantable supplemental parameter sensor 464 senses the one or more supplemental parameters. In the illustrated embodiment, implantable supplemental parameter sensors 464 includes a position sensor 482 that senses the position parameter indicative of whether the patient is in the supine position or the upright position.

ICD 401 is an embodiment of ICD 101 and includes a cardiac sensing circuit 463, an implant storage device 466, a hemodynamic signal processor 468, an implant control circuit 470, a pulse output circuit 472, and an implant telemetry circuit 474. Cardiac sensing circuit 463 senses one or more cardiac signals. In one embodiment, cardiac sensing circuit 463 senses an atrial electrogram and a ventricular electrogram through lead system 476, which includes, for example, leads 105 and 110. Implant storage device 466 stores the hemodynamic tolerability map generated by external system 102. Hemodynamic signal processor 468 processes the hemodynamic signals sensed by implantable hemodynamic sensor 462. In the illustrated embodiment, hemodynamic signal processor 468 includes a parameter generator 484 that generates the values of the one or more hemodynamic parameters using the one or more hemodynamic signals. In one embodiment, an external hemodynamic calibration system is provided to calibrate the values of the one or more hemodynamic parameters using environmental and/or non-invasive measurements. For example, an intravascular pressure is calibrated using ambient pressure sensed by an external barometer and/or another blood pressure measured by a non-invasive blood pressure sensor. In one embodiment, parameter generator 484 generates the values of the one or more hemodynamic parameters using the one or more hemodynamic signals and one or more other physiological signals acquired by ICD 401. The generated values of the one or more hemodynamic parameters are transmitted to external system 102 to be received by hemodynamic parameter input 228. Pulse output circuit 472 delivers cardiac stimulation pulses and includes a pacing output circuit 488 and a defibrillation output circuit 489. Pacing output circuit 488 is capable of delivering pacing pulses according to the hemodynamic challenge protocol and capable of delivering pacing pulses according to an ATP pacing mode. Defibrillation output circuit 489 delivers cardioversion and defibrillation pulses. Implant telemetry circuit 474 transmits data to and receives data from external system 102.

Implant control circuit 470 controls the operation of implantable system 460 including delivery of the cardiac stimulation pulses. In the illustrated embodiment, implant control circuit 470 includes a hemodynamic tolerability detector 485, a tachyarrhythmia detection and classification circuit 486, and a pulse delivery controller 487. Hemodynamic tolerability detector 485 detects the level of hemodynamic tolerability using at least the values of the one or more hemodynamic parameters generated by parameter generator 484 and the hemodynamic tolerability map stored in implant storage device 466. In one embodiment, hemodynamic tolerability detector 485 detects the level of hemodynamic tolerability using the values of the one or more hemodynamic parameters, the values of the one or more supplemental parameters sensed by implantable supplemental parameter sensors 464, and the hemodynamic tolerability map stored in implant storage device 466. Tachyarrhythmia detection and classification circuit 486 detects and classify tachyarrhythmia. Details of tachyarrhythmia detection and classification circuit 486 are discussed below, with reference to FIG. 5. In one embodiment, tachyarrhythmia detection and classification circuit 486 classifies each detected tachyarrhythmia as one of VT and SVT.

In response to the detection of tachyarrhythmia, the classification of the detected tachyarrhythmia and the detection of the level of hemodynamic tolerability are performed concurrently to provide pulse delivery controller 487 with a basis for determining whether and/or when to deliver one or more anti-tachyarrhythmia therapies. Pulse delivery controller 487 controls delivery of pacing, cardioversion, and defibrillation pulses. To generate the hemodynamic tolerability map, pulse delivery controller 487 controls delivery of pacing pulses according to the hemodynamic challenge protocol. After the hemodynamic tolerability map has been stored in implantable storage device 466, pulse delivery controller 487 controls delivery of pacing, cardioversion, and/or defibrillation pulses using the classification of the detected tachyarrhythmia and the detected level of hemodynamic tolerability. In one embodiment, a detected tachyarrhythmia associated with a low level of hemodynamic tolerability (less severe symptoms) is treated with a relatively conservative therapy, such as an ATP therapy, or a defibrillation therapy with a long delay before delivering a defibrillation pulse. The shock pulse is delivered only if the level of hemodynamic tolerability exceeds a certain threshold level or the classification of the detected tachyarrhythmia changes to one necessitating the delivery of the defibrillation pulse. A detected tachyarrhythmia with a high level of hemodynamic tolerability (more severe symptoms) is treated with a relatively aggressive therapy, such as an immediate defibrillation therapy, or a defibrillation therapy with a short delay before delivering the defibrillation pulse.

Figure 5:
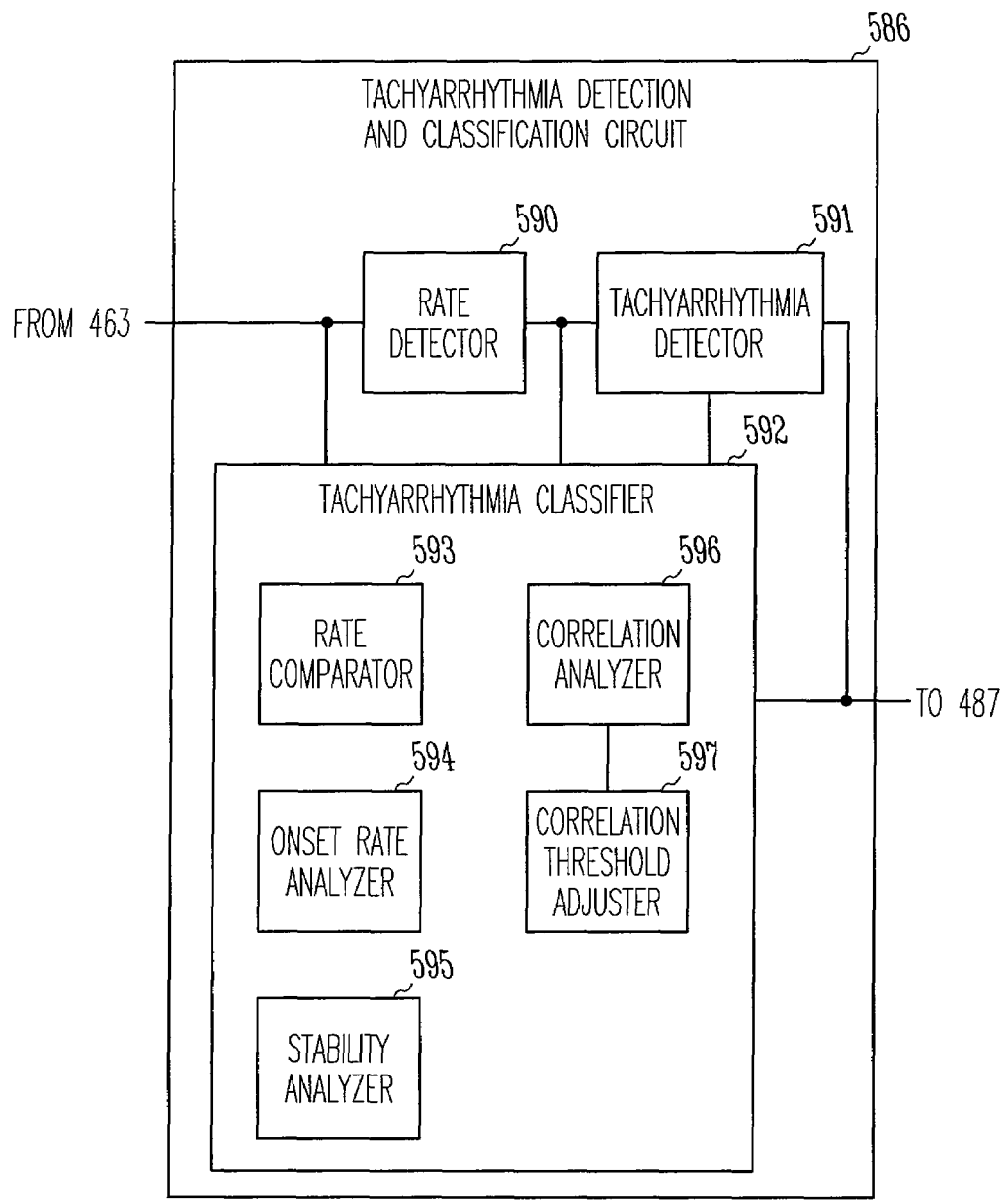
FIG. 5 is a block diagram illustrating an embodiment of a tachyarrhythmia detection and classification circuit.

FIG. 5 is a block diagram illustrating an embodiment of a tachyarrhythmia detection and classification circuit 586. Tachyarrhythmia detection and classification circuit 586 is an embodiment of tachyarrhythmia detection and classification circuit 486 and includes a rate detector 590, a tachyarrhythmia detector 591, and a tachyarrhythmia classifier 592.

Rate detector 590 receives one or more cardiac signals from cardiac sensing circuit 463 and detects one or more heart rates from the one or more cardiac signals. In one embodiment, rate detector 590 detects an atrial rate from an atrial electrogram and a ventricular rate from a ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 591 detects a tachyarrhythmia episode. In one embodiment, a tachyarrhythmia is detected when the ventricular rate exceeds a specified tachyarrhythmia threshold rate. In one embodiment, tachyarrhythmia detector 591 detects tachyarrhythmia by determining whether the ventricular rate is within one of a plurality of tachyarrhythmia rate zones each including a specified threshold rate. In a specific embodiment, the plurality of tachyarrhythmia rate zones includes a VF rate zone with a VF threshold rate programmable between 130 and 250 bpm, a fast VT rate zone with a fast VT threshold rate programmable between 110 and 210 bpm, and a slow VT rate zone with a slow VT threshold rate programmable between 90 and 200 bpm. In another embodiment, the tachyarrhythmia is detected using a "zoneless tachyarrhythmia detection" method, as discussed in U.S. patent application Ser. No. 11/301,716, "ZONELESS TACHYARRHYTHMIA DETECTION WITH REAL-TIME RHYTHM MONITORING", filed on Dec. 13, 2005, assigned to Cardiac Pacemakers, Inc., which is incorporated herein by reference in its entirety.

Tachyarrhythmia classifier 592 classifies each tachyarrhythmia detected by tachyarrhythmia detector 591. Examples of classification of tachyarrhythmia made by tachyarrhythmia classifier 592 include ventricular fibrillation (VF), ventricular tachycardia (VT), and supraventricular tachycardia (SVT), which includes atrial fibrillation (AF), atrial flutter (AFL), sinus tachycardia (ST), and atrial tachycardia (AT). In one embodiment, a detected tachyarrhythmia is classified as VF when the ventricular rate falls within the VF rate zone, without further analysis by tachyarrhythmia classifier 592. In the illustrated embodiment, tachyarrhythmia classifier 592 includes a rate comparator 593, an onset rate analyzer 594, a stability analyzer 595, a correlation analyzer 596, and a correlation threshold adjuster 597. Rate comparator 593 compares the atrial rate and the ventricular rate to determine whether the atrial rate exceeds, equals, or is lower than the ventricular rate by a specified margin. Onset rate analyzer 594 produces an onset rate of the detected tachyarrhythmia and determines whether the detected tachyarrhythmia has a gradual onset or a sudden onset by comparing the onset rate to one or more threshold onset rates. The onset rate is a rate of transition of the ventricular rate from a normal sinus rate to a tachyarrhythmic rate when the detected tachyarrhythmia begins. A gradual onset indicates a physiological tachyarrhythmia, such as an ST caused by exercise. A sudden onset indicates a pathological tachyarrhythmia. Stability analyzer 595 produces a rate stability parameter indicative of a degree of heart rate variability and determines whether the heart rate is stable by comparing the stability parameter to a stability threshold. In one embodiment, the stability parameter is produced as an average variance of a series of cardiac intervals. In one embodiment, stability analyzer 595 produces a ventricular rate stability parameter and an atrial stability parameter. The ventricular rate stability parameter is indicative of a degree of ventricular rate variability. The atrial stability parameter is indicative of a degree of atrial rate variability. Stability analyzer 595 determines whether the ventricular rate is stable by comparing the ventricular rate stability parameter to a ventricular stability threshold and determines whether the atrial rate is stable by comparing the atrial stability parameter to an atrial stability threshold. In one embodiment, stability analyzer 595 compares the ventricular rate stability parameter and the atrial stability parameter to determine which of the ventricular rate and the atrial rate is more stable. Correlation analyzer 596 analyzes a correlation between a tachyarrhythmic waveform and a template waveform and produces a correlation coefficient representative of that correlation. The tachyarrhythmic waveform includes a segment of a cardiac signal sensed during the detected tachyarrhythmia. The template waveform is recorded during a known cardiac rhythm such as the normal sinus rhythm (NSR). One example for producing such a correlation coefficient, referred to as a feature correlation coefficient (FCC), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. In one embodiment, the detected tachyarrhythmia is considered as "correlated" if a correlation coefficient exceeds a correlation threshold and as "marginally correlated" if the correlation coefficient exceeds a marginal correlation threshold that is lower than the correlation threshold. Correlation threshold adjuster 597 allows adjustment of the correlation threshold and/or the marginal correlation threshold. Tachyarrhythmia classifier 346 classifies the detected tachyarrhythmia using one or more of the atrial rate, ventricular rate, onset rate, stability parameter, and correlation coefficient.

In one embodiment, tachyarrhythmia classifier 592 classifies the detected tachyarrhythmia using a method discussed below with reference to FIG. 6. The classification of the detected tachyarrhythmia, as well as the various characteristics such as the atrial rate, ventricular rate, onset rate, stability parameter, and correlation coefficient, are used for selecting a suitable anti-tachyarrhythmia therapy.

Figure 6:
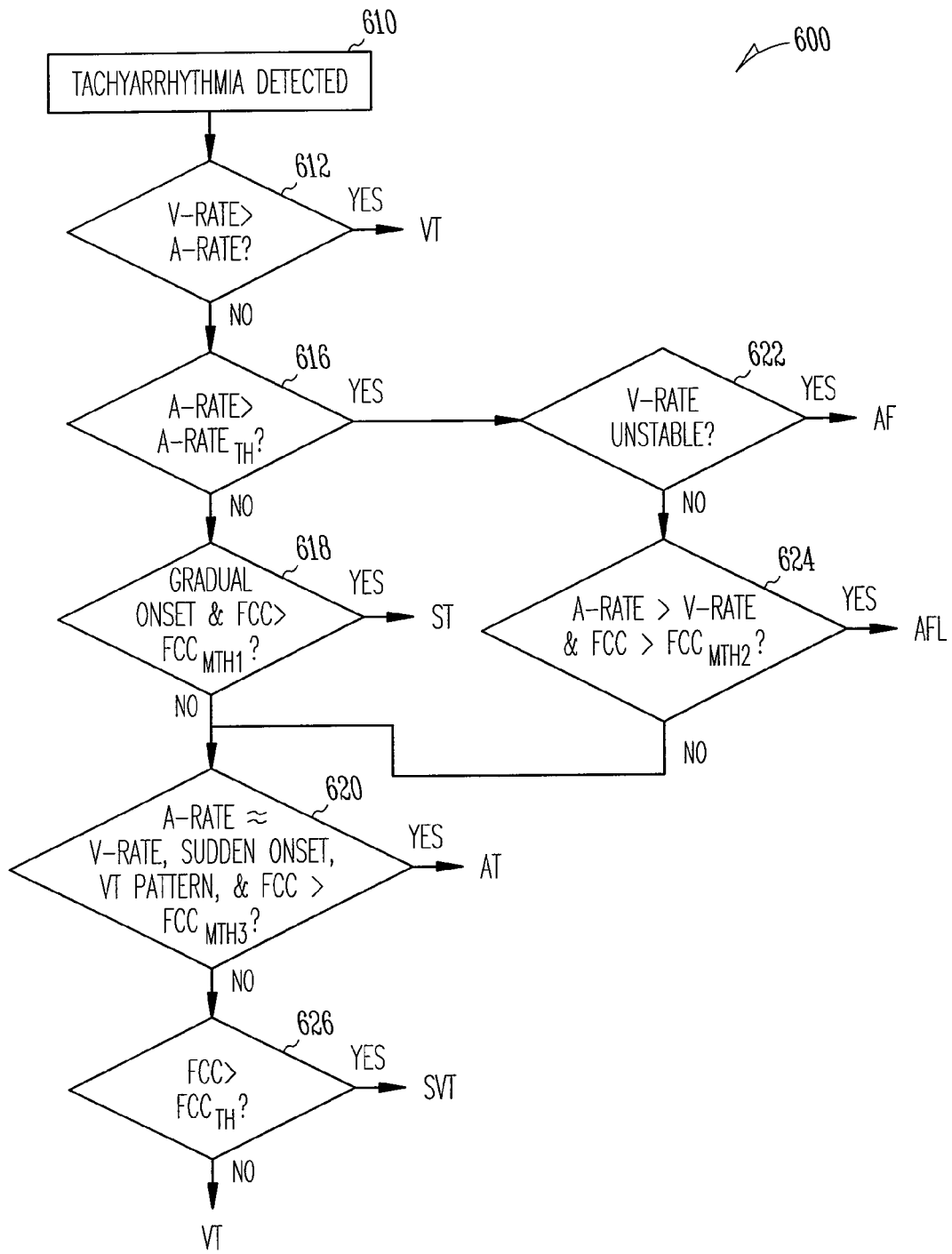
FIG. 6 is a flow chart illustrating an embodiment of a method for classifying a detected tachyarrhythmia.

FIG. 6 is a flow chart illustrating an embodiment of a method 600 for classifying a detected tachyarrhythmia. In one embodiment, tachyarrhythmia classifier 592 performs method 600. The atrial rate, ventricular rate, onset rate, stability parameter, correlation coefficient, and various thresholds used in method 600 are detected, produced, or programmed as discussed with reference to FIG. 5 above. For correlation analysis, the template waveform is produced using a cardiac signal sensed during an NSR.

A tachyarrhythmia is detected at 610, when the ventricular rate is within a specified tachyarrhythmia rate zone. If the ventricular rate (V-RATE) exceeds the atrial rate (A-RATE) by a specified margin at 612, the detected tachyarrhythmia is classified as VT. In one embodiment, the specific margin is about 10 bpm. If the ventricular rate does not exceed the atrial rate by the specified margin at 612, the atrial rate is compared to a threshold atrial rate (A-RATE$_{TH}$) at 616.

If the atrial rate does not exceed the threshold atrial rate at 616, the onset rate indicates a gradual onset of tachyarrhythmia at 618, and the correlation coefficient (FCC) exceeds a first marginal correlation threshold (FCC$_{MTH1}$) (i.e., FCC falls between FCC$_{MTH1}$ and FCC$_{TH}$) at 618, the detected tachyarrhythmia is classified as ST. ST is a physiologic tachyarrhythmia originated in an SA node when the SA node generates the electrical impulses at a tachyarrhythmic rate. In one embodiment, the first marginal correlation coefficient is programmable between 0.4 and the correlation threshold (i.e., $0.4 \leq FCC_{MTH1} \leq FCC_{TH}$), with approximately 0.8 being a specific example. In one embodiment, the first marginal correlation threshold is set to be lower than the correlation threshold by a specified amount, such as approximately 0.2 (i.e., FCC$_{MTH1}$≈FCC$_{TH}$−0.2).

If the atrial rate exceeds the threshold atrial rate at 616, and the ventricular rate is unstable at 622, the detected tachyarrhythmia is classified as AF. If the ventricular rate is stable at 622, the atrial rate exceeds the ventricular rate by the specified margin, and the correlation coefficient exceeds a second marginal correlation threshold (FCC$_{MTH2}$) (i.e., FCC falls between FCC$_{MTH2}$ and FCC$_{TH}$) at 624, the detected tachyarrhythmia is classified as AFL. In one embodiment, the second marginal correlation threshold is programmable between 0.4 and the correlation threshold (i.e., $0.4 \leq FCC_{MTH2} \leq FCC_{TH}$), with approximately 0.8 being a specific example. In one embodiment, the second marginal correlation threshold is set to be lower than the correlation threshold by a specified amount, such as approximately 0.2 (i.e., FCC$_{MTH2}$≈FCC$_{TH}$−0.2).

If the atrial rate approximately equals to the ventricular rate, the onset rate indicates a sudden onset of tachyarrhythmia, the atrial and ventricular events occur in a specified SVT pattern, and the correlation coefficient exceeds a third marginal correlation threshold (FCC$_{MTH3}$) (i.e., FCC falls between FCC$_{MTH3}$ and FCC$_{TH}$) at 620, the detected tachyarrhythmia is classified as AT. In one embodiment, the atrial rate is considered to be approximately equal to the ventricular rate when the difference between the two rates is below 10 bpm. The detection of cardiac event patterns including the SVT pattern is discussed in U.S. patent application Ser. No. 11/276,213, entitled "RHYTHM DISCRIMINATION OF SUDDEN ONSET AND ONE-TO-ONE TACHYARRHYTHMIA", filed on Feb. 17, 2006, assigned to Cardiac Pacemakers, Inc., which is hereby incorporated in its entirety. If these conditions are not met at 620, the correlation coefficient is compared to the correlation threshold (FCC$_{TH}$) at 626. AT is a pathologic tachyarrhythmia that occurs when a biologic pacemaker (focus) in an atrium usurps control of the heart rate from the SA node. In one embodiment, the third marginal correlation threshold is programmable between 0.4 and the correlation threshold (i.e., $0.4 \leq FCC_{MTH3} \leq FCC_{TH}$), with approximately 0.6 being a specific example. In one embodiment, the third marginal correlation threshold is set to be lower than the correlation threshold by a specified amount, such as approximately 0.4 (i.e., $FCC_{MTH3} \approx FCC_{TH} - 0.4$).

If the correlation coefficient exceeds the correlation threshold at 626, the detected tachyarrhythmia is classified as SVT. If the correlation coefficient does not exceed the correlation threshold at 626, the detected tachyarrhythmia is classified as VT. In one embodiment, the correlation threshold is programmable between 0.6 and 0.99, with approximately 0.94 being a specific example.

Figure 7:
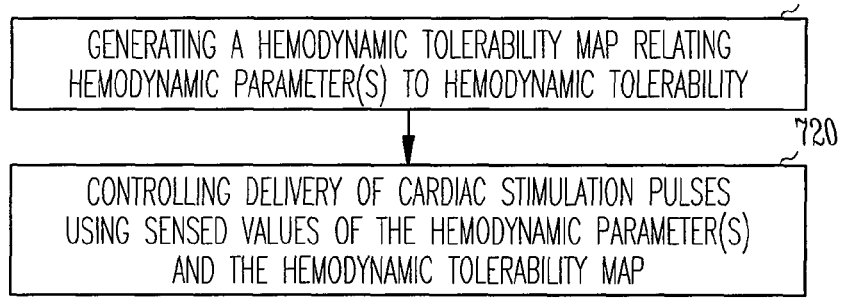
FIG. 7 is a flow chart illustrating an embodiment of a method for controlling delivery of anti-tachyarrhythmia therapy.

FIG. 7 is a flow chart illustrating an embodiment of a method 700 for controlling delivery of anti-tachyarrhythmia therapy. In one embodiment, method 700 is performed using CRM system 100, including its various embodiments discussed in this document.

A hemodynamic tolerability map relating at least values of one or more hemodynamic parameters to levels of hemodynamic tolerability is generated at 710. In one embodiment, the hemodynamic tolerability map is generated using an external system, such as an implantable medical device programmer, that communicates with an implantable medical device, such as an ICD. The values of the one or more hemodynamic parameters are sensed using implantable hemodynamic sensors that are part of, or coupled to, the implantable medical device. The generation of the hemodynamic tolerability map is further discussed below, with reference to FIG. 8. In various embodiments, the hemodynamic tolerability map is in any format that is capable of representing the relationship between at least the values of the one or more hemodynamic parameters and the levels of hemodynamic tolerability.

Delivery of cardiac stimulation pulses is controlled using sensed values of the one or more hemodynamic parameters and the hemodynamic tolerability map at 720. In one embodiment, the cardiac stimulation pulses include pacing, cardioversion, and/or defibrillation pulses delivered from the implantable medical device. The control of delivery of cardiac stimulation pulses is further discussed below, with reference to FIG. 9.

Figure 8:
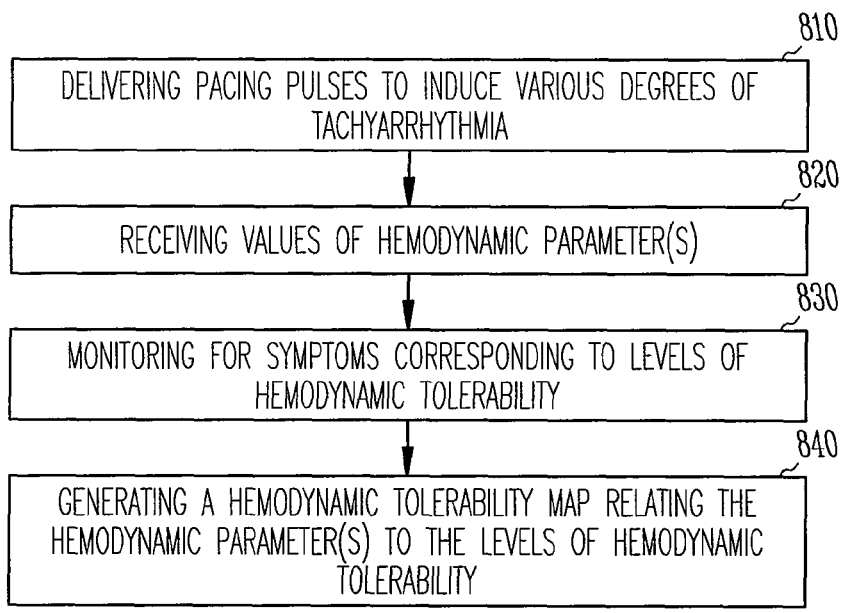
FIG. 8 is a flow chart illustrating an embodiment of a method for generating a hemodynamic tolerability map.

FIG. 8 is a flow chart illustrating an embodiment of a method 800 for generating the hemodynamic tolerability map. In one embodiment, method 800 is performed using hemodynamic tolerability map generating system 122, including its various embodiments discussed in this document.

Pacing pulses are delivered to a patient to induce various degrees of tachyarrhythmia in the patient at 810. In one embodiment, the pacing pulses are delivered from an ICD with pacing capabilities implanted in the patient. The ICD is programmed to control the delivery of the pacing pulses by executing a hemodynamic challenge protocol. The hemodynamic challenge protocol is produced to induce increasingly severe tachyarrhythmia by delivering the pacing pulses at an increasing pacing rate. In one embodiment, in addition to delivering the pacing pulses, the hemodynamic challenge protocol uses other means such as defibrillation shocks, exercise, and psychological stress to induce various symptoms for evaluating the patient's hemodynamic tolerability.

Values of one or more hemodynamic parameters are received at 820. These values are sensed during the delivery of the pacing pulses. In one embodiment, the one or more hemodynamic parameters are sensed by implantable sensors in or connected to the ICD during the execution of the hemodynamic challenge protocol and transmitted to an external device such as a programmer communicating with the ICD. Examples of such hemodynamic parameters include parameters derived from intracardiac impedance, transthoracic impedance, arterial pressure, PAP, RV pressure, LV coronary pressure, LV coronary temperature, and level of blood oxygen saturation, such as the amplitude, derivative (rate of change), and morphology of each of these signals. In one embodiment, the one or more hemodynamic parameters include stroke impedance, which is the difference between a maximum value and a minimum value of the intracardiac or transthoracic impedance over a cardiac cycle. In one embodiment, the one or more hemodynamic parameters include a composite hemodynamic parameter calculated using a plurality of hemodynamic parameters. In a specific embodiment, the composite hemodynamic parameter is calculated using the plurality of hemodynamic parameters and a plurality of weighting factors each associated with a hemodynamic parameter of the plurality of hemodynamic parameters. In one embodiment, the hemodynamic parameters include parameters derived from one or more hemodynamic signals and one or more other physiological signals. In one embodiment, in addition to receiving the values of the one or more hemodynamic parameters, values of one or more supplemental parameters are concurrently received at 820. The one or more supplemental parameters affect the sensed values of the one or more hemodynamic parameter and/or the level of hemodynamic tolerability. One example of a supplemental parameter is a position parameter indicative of whether the patient is in a supine position or an upright position.

Symptoms corresponding to the levels of hemodynamic tolerability are monitored at 830. Examples of such symptoms include dizziness, angina, weakness, and syncope. When each symptom or its known indication is perceived by the patient and/or observed by a physician or other caregiver, annotation is made by the physician or other caregiver and recorded in association with the one or more hemodynamic parameters. The annotations allow association between the levels of the patient's hemodynamic tolerability and the values of the one or more hemodynamic parameters sensed from the patient. In one embodiment, the annotations include markers each indicative a level of the patient's hemodynamic tolerability. In another embodiment, the annotations also include text entered by the physician or other caregiver.

A hemodynamic tolerability map relating at least the received values of the one or more hemodynamic parameters to the levels of hemodynamic tolerability is generated at 840. The hemodynamic tolerability map is generated for each individual patient using the results of executing the hemodynamic challenge protocol for that patient. In one embodiment, the hemodynamic tolerability map relates the values of the one or more hemodynamic parameters and values of the one or more supplemental parameters to the levels of hemodynamic tolerability. In one embodiment, the values of the one or more hemodynamic parameters used to generate the hemodynamic tolerability map include values estimated by extrapolation using the sensed values of the one or more hemodynamic parameters for patient safety and/or comfort.

Figure 9:
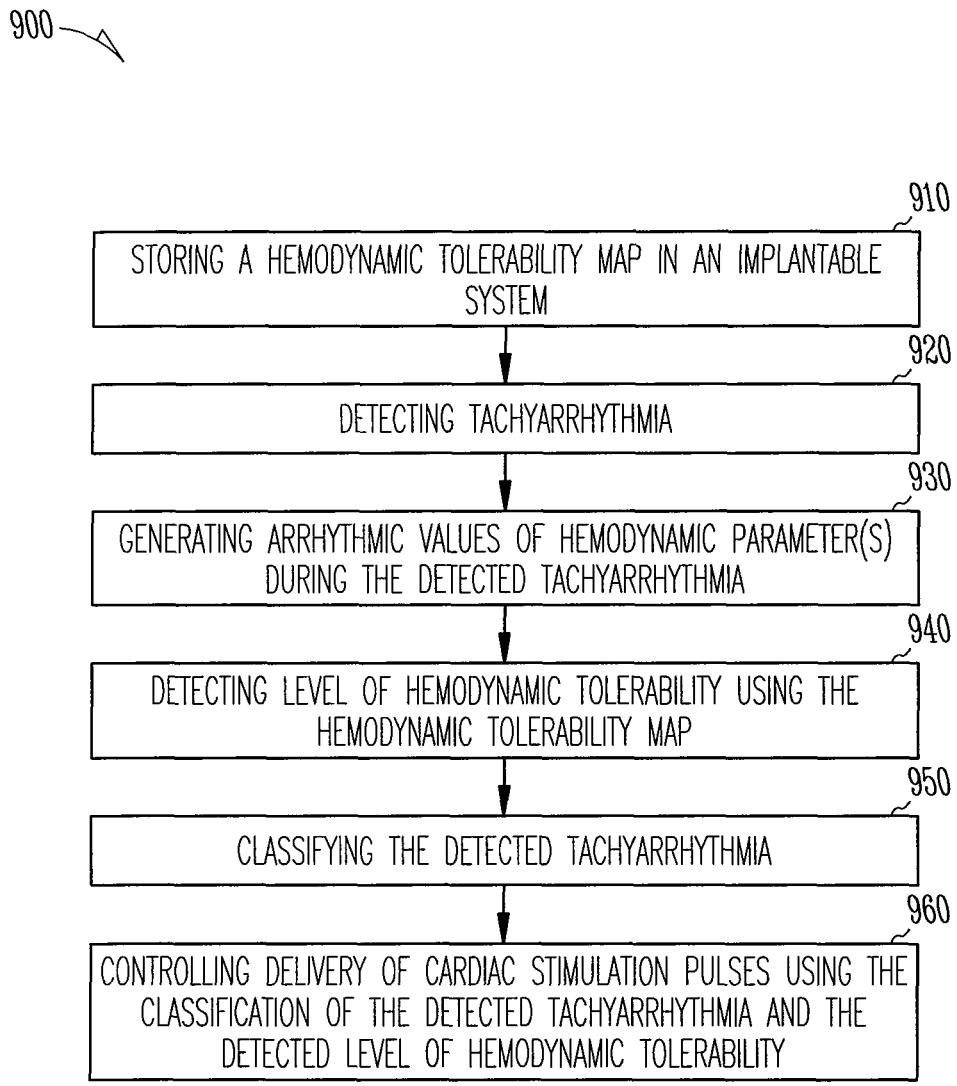
FIG. 9 is a flow chart illustrating an embodiment of a method for controlling delivery of anti-tachyarrhythmia therapy using the hemodynamic tolerability map.

FIG. 9 is a flow chart illustrating an embodiment of a method 900 for controlling delivery of anti-tachyarrhythmia therapy using the hemodynamic tolerability map. In one embodiment, method 900 is performed using the implantable system of CRM system 100, including its various embodiments discussed in this document.

The hemodynamic tolerability map is stored in the implantable system, such as in the ICD used to deliver the pacing pulses during the execution of the hemodynamic challenge protocol, at 910. Tachyarrhythmia is detected at 920, such as by using one or more heart rates of the patient. Arrhythmic values of the one or more hemodynamic parameters are generated during the detected tachyarrhythmia at 930. The patient's level of hemodynamic tolerability is detected using at least the arrhythmic values of the one or more hemodynamic parameters and the stored hemodynamic tolerability map at 940. In one embodiment, the hemodynamic tolerability map relates threshold values of the one or more hemodynamic parameters to the levels of hemodynamic tolerability. In other words, the threshold values of the one or more hemodynamic parameters each specify one of the levels of hemodynamic tolerability. The level of the patient's hemodynamic tolerability is detected by comparing the arrhythmic values of the one or more hemodynamic parameters to threshold values of the one or more hemodynamic parameters. In one embodiment, in which the hemodynamic tolerability map relates the values of the one or more hemodynamic parameters and the values of the one or more supplemental parameters to the levels of hemodynamic tolerability, arrhythmic values of the one or more supplemental parameters are also generated during the detected tachyarrhythmia at 930. The level of hemodynamic tolerability is detected at 940 using the arrhythmic values of the one or more hemodynamic parameters, the arrhythmic values of one or more supplemental parameters, and the stored hemodynamic tolerability map. The detected tachyarrhythmia is classified at 950, concurrently with the detecting the level of hemodynamic tolerability. In one embodiment, the detected tachyarrhythmia is classified using method 600 or selected steps of that method.

Delivery of cardiac stimulation pulses from the implantable system is controlled using the classification of the detected tachyarrhythmia and the detected level of hemodynamic tolerability at 960. In various embodiments, the cardiac stimulation pulses include pacing, cardioversion, and/or defibrillation pulses. If the detected level of hemodynamic tolerability is relatively low, the detected tachyarrhythmia is treated with a relatively conservative therapy, such as an ATP therapy and a defibrillation therapy with a long delay before delivering the therapy. If the detected level of hemodynamic tolerability is relatively high, the detected tachyarrhythmia with high level of hemodynamic tolerability (more severe symptoms) is treated with a relatively aggressive therapy, such as a defibrillation therapy with no or relatively short delay before delivering the defibrillation pulse.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system, comprising:
    a hemodynamic tolerability analyzer including:
        a hemodynamic parameter input configured to receive values of one or more hemodynamic parameters including values of the one or more hemodynamic parameters sensed during delivery of pacing pulses according to a hemodynamic challenge protocol, the hemodynamic challenge protocol specifying an incrementally increasing pacing rate such that the pacing pulses are delivered to induce increasingly severe tachyarrhythmia;
        an annotation input configured to receive annotations associating the values of the one or more hemodynamic parameters to levels of hemodynamic tolerability each being a measure of tolerance to deteriorated hemodynamic performance resulting from tachyarrhythmia; and
        a hemodynamic tolerability map generator configured to generate a hemodynamic tolerability map relating at least the values of the one or more hemodynamic parameters to the levels of hemodynamic tolerability; and
    a control circuit configured to control the delivery of pacing pulses by executing the hemodynamic challenge protocol.

2. The system of claim 1, wherein the hemodynamic tolerability map generator is configured to generate a hemodynamic tolerability map relating at least the values of the one or more hemodynamic parameters to specified type hemodynamically compromising symptoms each corresponding to one of the levels of hemodynamic tolerability.

3. The system of claim 2, wherein the hemodynamic tolerability map generator is configured to generate a hemodynamic tolerability map relating threshold values of the one or more hemodynamic parameters to the levels of hemodynamic tolerability.

4. The system of claim 2, wherein the hemodynamic tolerability map generator is configured to:
    extrapolate additional values of the one or more hemodynamic parameters using the received values of the one or more hemodynamic parameters; and
    generate a hemodynamic tolerability map relating at least the received values and the extrapolated additional values of the one or more hemodynamic parameters to the levels of hemodynamic tolerability.

5. The system of claim 1, comprising an external system including:
    the hemodynamic tolerability analyzer;
    the control circuit; and
    an external telemetry circuit configured to transmit data to and receive data from an implantable system via a telemetry link.

6. The system of claim 5, wherein the external system comprises a user interface including a user input device configured to receive the annotations and record the received in association with the received values of the one or more hemodynamic parameters.

7. The system of claim 6, wherein the user interface comprises a presentation device to present the annotations and the received values of the one or more hemodynamic parameters.

8. The system of claim 7, wherein the presentation device comprises one or more of a display screen and a printer.

9. The system of claim 6, wherein the user input device comprises one or more mechanical push buttons or one or more buttons displayed on an interactive screen, each of the mechanical push buttons or the buttons on the interactive screen corresponding to one of the levels of hemodynamic tolerability.

10. The system of claim 5, comprising the implantable system, including:
    an implant telemetry circuit configured to transmit data to and receive data from the external system;
    one or more implantable hemodynamic sensors configured to sense one or more hemodynamic signals;
    a pacing output circuit to deliver the pacing pulses; and
    a pulse delivery controller configured to control the delivery of the pacing pulses by executing the hemodynamic challenge protocol.

11. The system of claim 10, wherein the one or more implantable hemodynamic sensors comprise one or more of:
    an impedance sensor configured to sense an impedance signal;
    a pressure sensor configured to sense a blood pressure signal;

a temperature sensor configured to sense a blood temperature signal; and
a pulse oximeter configured to sense an oximetry signal indicative of the level of blood oxygen saturation,
and comprising a parameter generator configured to generate the one or more hemodynamic parameters using the one or more of the impedance signal, blood pressure signal, blood temperature signal, and oximetry signal.

12. The system of claim 11, wherein the parameter generator is configured to generate a composite hemodynamic parameter calculated using a plurality of hemodynamic parameters including the impedance signal, blood pressure signal, blood temperature signal, and oximetry signal.

13. The system of claim 11, wherein the hemodynamic tolerability analyzer comprises a supplemental parameter input configured to receive values of at least a position parameter, and the hemodynamic tolerability map generator is configured to generate a hemodynamic tolerability map relating the values of at least one or more hemodynamic parameters and the values of at least the position parameter to the levels of hemodynamic tolerability.

14. The system of claim 10, wherein the implantable system comprises:
a parameter generator configured to generate the one or more hemodynamic parameters using the one or more hemodynamic signals;
a storage circuit configured to store the hemodynamic tolerability map generated by the external system and transmitted to the implantable system via telemetry; and
a hemodynamic tolerability detector to detect the level of hemodynamic tolerability using at least the one or more hemodynamic parameters and the stored hemodynamic tolerability map.

15. The system of claim 14, wherein the implantable system comprises:
a defibrillation output circuit configured to deliver defibrillation pulses; and
a tachyarrhythmia detection and classification circuit configured to detect and classify tachyarrhythmia,
and wherein the pulse delivery controller is configured to control delivery of the pacing pulses and defibrillation pulses using a classification of a tachyarrhythmia and the level of hemodynamic tolerability detected during the tachyarrhythmia.

16. The system of claim 15, wherein the tachyarrhythmia detection and classification circuit comprises a rate detector configured to detect a ventricular rate and an atrial rate, a tachyarrhythmia detector configured to compare the detected ventricular rate to a tachyarrhythmia rate threshold, and a tachyarrhythmia classifier comprising one or more of:
a rate comparator configured to compare the detected ventricular rate to the detected atrial rate;
an onset rate analyzer configured to detect a rate of transition of the sensed ventricular rate;
a stability analyzer configured to detect a stability of heart rate;
a correlation analyzer configured to analyze a correlation between a tachyarrhythmia waveform and a template waveform; and
a correlation threshold adjuster configured to adjust a correlation threshold or a marginal correlation threshold.

17. The system of claim 16, wherein the correlation analyzer is configured to compute a correlation coefficient between a tachyarrhythmia waveform and a template waveform, the template waveform recorded during a known cardiac rhythm such as a normal sinus rhythm (NSR).

18. The system of claim 14, wherein the storage circuit is configured to update the stored hemodynamic tolerability map using information recorded during the use of the implantable system.

19. The system of claim 15, wherein the tachyarrhythmia detection and classification circuit is configured to discriminate the detected tachyarrhythmia into one of a ventricular fibrillation (VF), a ventricular tachycardia (VT), or a supraventricular tachycardia (SVT), the SVT including an atrial fibrillation (AF), an atrial flutter (AFL), a sinus tachycardia (ST), and an atrial tachycardia (AT).

20. The system of claim 15, wherein the pulse delivery controller is configured to control the defibrillation output circuit to deliver defibrillation pulses in response to the level of hemodynamic tolerability exceeding a certain threshold level or the detected tachyarrhythmia being classified as VT or VF.

21. The system of claim 20, wherein the pulse delivery controller is configured to deliver an anti-tachycardia pacing (ATP) in response to a specified level of hemodynamic tolerability.

22. The system of claim 20, wherein the pulse delivery controller is configured to control a time delay before delivering the defibrillation pulse, the time delay determined using the level of hemodynamic tolerability.

23. The system of claim 10, wherein the implantable system comprises:
a defibrillation circuit to deliver defibrillation shocks; and
a defibrillation delivery controller configured to control the delivery of the defibrillation shocks by executing the hemodynamic challenge protocol.

24. The system of claim 10, wherein the implantable system comprises:
a cardioversion circuit to deliver cardioversion shocks; and
a cardioversion delivery controller configured to control the delivery of the cardioversion shocks by executing the hemodynamic challenge protocol.

* * * * *